United States Patent [19]

Sakamoto et al.

[11] Patent Number: 4,655,211

[45] Date of Patent: Apr. 7, 1987

[54] HEMOSTATIC AGENT

[75] Inventors: Izumi Sakamoto; Tukasa Unigame; Kunihiko Takagi, all of Kyoto, Japan

[73] Assignee: Unitika Ltd., Hyogo, Japan

[21] Appl. No.: 763,589

[22] Filed: Aug. 8, 1985

[30] Foreign Application Priority Data

Aug. 9, 1984 [JP] Japan .................................. 59-166884

[51] Int. Cl.$^4$ .............................................. A61L 15/00
[52] U.S. Cl. ..................................... 128/156; 128/325
[58] Field of Search ................................. 128/156, 325

[56] References Cited

U.S. PATENT DOCUMENTS

| | | | |
|---|---|---|---|
| 2,533,004 | 12/1950 | Ferry et al. ........................... | 128/156 |
| 3,249,109 | 5/1966 | Maeth et al. ......................... | 128/156 |
| 3,419,006 | 12/1968 | King ..................................... | 128/156 |
| 4,265,233 | 5/1981 | Sugitachi et al. ..................... | 128/156 |
| 4,271,070 | 6/1981 | Miyata et al. ........................ | 128/156.0 |

FOREIGN PATENT DOCUMENTS 2914822  10/1979  Fed. Rep. of Germany ...... 128/156

*Primary Examiner*—E. Rollins Cross
*Attorney, Agent, or Firm*—Sughrue, Mion, Zinn, Macpeak & Seas

[57] ABSTRACT

A hemostatic agent and method for preparation thereof are described, said hemostatic agent comprising a carrier in the shape of flake or fiber having thrombin and Factor XIII fixed thereto, wherein said carrier is composed of a biodegradable material having a water absorption capability of about 50 weight percent or more, said flake has a longer dimension of about 5000 microns or less, a shorter dimension of about 3000 microns or less, and a thickness of about 2000 microns or less, and said fiber has a single yarn fineness of about 30 deniers or less and a yarn length of about 10 mm or less.

12 Claims, No Drawings

HEMOSTATIC AGENT

FIELD OF THE INVENTION

This invention relates to a hemostatic agent. In more detail, the invention relates to a hemostatic agent suitable particularly as the agent for hemostasis after therapy or diagnosis, as in the case of direct puncture or biopsy.

BACKGROUND OF THE INVENTION

In recent years, therapies including direct puncture and biopsy in the medical field have been numerously performed, but in such cases, hemorrhage is inevitably induced, and it is clinically very important to stop the bleeding promptly. Since direct puncture or biopsy damages the blood vessels, hemorrhage from the injured site is inevitably caused, and if this bleeding continues for many hours, death may result. Accordingly, it is important to stop such bleeding promptly and surely.

However, no fully satisfactory hemostatic agent for such bleeding is known at present. That is, no hemostatic agent is known that can stop the bleeding from the injured site to the lacuna (pit) produced at the body-tissue or viscera by puncture or biopsy by easy filling of the lacuna with sol-like substance.

Reasons why such hemostatics have not so far been produced is that, according to the general theories of hemostatic therapy, it is to be better in the use of hemostatic materials under dry state, or that it is necessary to apply strong compression to the bleeding site.

In view of the above theories, it would never be favorably considered to use a sol-type agent for administration of hemostatics, and thus sol-type has never been considered to exert an appropriate hemostatic effect, and thus a sol-type agent has not been adopted for actual clinical practices. At present, for the hemostasis of the above mentioned bleeding, a rod-like material referred to as a "sounding" or inner tube of a biopsy needle or puncture needle is inserted to obtain physical stoppage of the bleeding hemostasis by forming a blood clot. Such a method requires a long time for completing hemostasis, and sometimes complete hemostasis cannot be obtained; that is, even when the hemostatic function of the patient is normal, it is not certain that complete hemostasis will be achieved even after continuing compression for 10-15 minutes. Further, it is not certain that the accident (accidental death) due to the bleeding (after bleeding) for a long time will be prevented. Moreover, the above technique may not achieve hemostasis in patients with reduced hemostatic function.

In the patient with reduced hemostatic function, there may be the case that hemostasis cannot be achieved and that the direct puncture and biopsy themselves should be abondoned.

Accordingly, the production of a hemostatic agent for obtaining prompt and complete hemostasis has been eagerly waited.

For obtaining such hemostatic agents, there are several types of techniques.

U.S. Pat. No. 4,265,233 refers to the exerting effect of fixing Factor XIII with thrombin to gelatin as a wound heeling material by accelerating the formation of insoluble fibrin; however, there is no mention of the hemostatic effect.

*Trans. Am. Soi. Artif. Intern. Organs*, Vol. XXVIII, 1982, pp464–468 and *J. J. Artificial Organs* (Jinko Zoki), Vol. 10, No. 6, 1981, pp1079–1082; Vol. 11, No. 6, 1982, pp958–961 describes the use of the gelatin material on which Factor XIII and thrombin are fixed as a suitable occluding material for transcatheter embolization; that is, an absorbable gelatin sponge (e.g., Spongel, trademark of Yamanouchi Pharm. (5×2.5×0.5 cm)) is fixed with thrombin and Factor XIII, then sliced, followed by mixing with contrast medium to form a sol-material, and using it as occluding material. However, this method accelerates insoluble fibrinformation by infusing the material into the blood vessel through an angiographic catheter. Thus, it does not suggest the performance of hemostasis by applying this agent for bleeding at a lacuna-site from the injured blood vessel by administration into micro-lacunae or pits (pores) occurring in the tissues or viscera. In the above mentioned *J. J. Jinko Zoki*, Vol. 11, No. 6, 1982, p.959, it is simply noted that it is applicable as a topical hemostatic material among its possibilities for clinical application. Whereas the administration method estimated from this phrase is similar to the usual administration method of Spongel (trademark) used as carrier, that is, this material formed in the shape of a dry cuboid is pressee and attached on the bleeding site, and it does not contain any hint of a method to treat the hemorrhage after an operation with direct puncture or biopsy. As mentioned in the above, by the conventional techniques, there is no review and no clarification of the optimum state for hemostasis in the bleeding after direct puncture and/or biopsy.

SUMMARY OF THE INVENTION

This invention is intended to provide a hemostatic agent particularly suitable for hemostasis after an operation with direct punctur or biopsy. For achieving such objectives, extensive research has been conducted and, as a result, the hemostasis agent produced by the fixation of Factor XIII and thrombin to a carrier in the specific shape of the biodegradable material (a substance absorbable in living tissues) having a water absorption capability of 50 weight percent or more has demonstrated the following features.

(A) Sol-formation can be promptly conducted by mixing the material with a medium such as physiological saline solution and aqueous calcium chloride solution, etc., and it is easily infused into the bleeding site through a puncture needle or biopsy needle.

(B) Since this is a sol-form with water as a medium, the compression effect against hemorrhage is lower, and yet, it shows excellent hemostatic effect.

(C) This hemostatic effect is observed multiplicatively or synergically only under the presence of both thrombin and Factor XIII.

Thus, the present invention is directed to a hemostatic agent comprising a carries in the shape of flake or fiber having thrombin and Factor XIII fixed thereto, wherein said carrier is composed of a biodegradable material having a water absorption capability of about 50 weight percent or more, said flake has a longer dimension of about 5,000 microns or less, a shorter dimension of about 3,000 microns or less, and a thickness of about 2,000 microns or less, and said fiber has a single yarn fineness of about 30 deniers or less and a yarn length of about 10 mm or less.

For a main use of the hemostatis agent of this invention, the agent is mixed with media such as physiological saline solution or aqueous solution of $CaCl_2$ for sol-formation, which is infused into a bleeding site by direct puncture or biopsy through a puncture-needle or biopsy needle.

DETAILED DESCRIPTION OF THE INVENTION

Biodegradable material according to this invention should have a water-absorption capability of about 50 weight percent or more. When the water-absorption capability is less than about 50 weight percent, if it is mixed with a medium like water, the material is not transformed to an injectable sol-form promptly, e.g., within 2-3 minutes, and thus it is not suitable. On the other hand, a preferable water-absorption capability is less than 1000 weight percent, and that less than 500 weight percent is more preferable.

It is difficult to obtain the smoothly injectable sol-form in the case of an excessively high water-absorption capability. Herein, water-absorption capability is defined by the formula shown the below.

Water-absorption capability (weight percent) =

$$\frac{\left(\begin{array}{c}\text{Weight after soaking} \\ \text{for 3 minutes in water 25° C.}\end{array} - \begin{array}{c}\text{Weight before} \\ \text{soaking in water}\end{array}\right)}{\text{Weight before soaking in water}} \times 100$$

Said carrier material constituting the hemostatic agent of this invention should have a biodegradable property being absorbed into the living tissue so that there is no necessity of further action such as removal thereof after the initial application to the affected site.

Preferable materials for this purpose include collagen, gelatin chitin, fibrinogen, polyglycolic acid, polylactic acid, glycolic acid-lactic acid copolymer, polyglutamic acid, amylose, and oxidized amylose. Gelatin, collagen and chitin are espesially favorably used.

For the carrier of the flake type used in this invention, the longer dimension is generally about 5000 microns or less, and preferably is from 200 to 1000 microns, the shorter dimension is generally about 3000 microns or less, and preferably is from 200 to 800 microns, and the thickness is generally about 2000 microns or less, preferably is 800 microns or less, and more preferably is from 50-800 microns (including micro-grain type).

For the carrier of the fiber type used in this invention, the finess of a single yarn thereof is generally about 30 deniers or less, and preferably is from 0.5 to 15 deniers, and the yarn length is generally about 10 mm or less, preferably is less than 3 mm and more preferably is from 50 to 3000 microns.

Outside of the foregoing values, it is difficult to obtain a uniform sol-state by the media such as physiological saline solution, etc., and, also, clogging will tend to occur because sol-state substance does not pass through the syringe or catheter smoothly. Especially, substances with higher values than the above levels will tend to be defective when smooth flow is required through a syringe of 23-gauge, 25-gauge, or thinner diameters.

Thrombin used for this invention is a protainase to convert fibrinogen into fibrin. Thrombin is isolated from human, bovine, swine blood, and the like. While in application for the treatment of man, it is preferable to use human thrombin.

Factor XIII (also referred to as FXIII) used for this invention is called fibrin-stabilizing factor, and it directly acts on non-stabilizing fibrin, being involved in the formation of isopeptide bond among fibrin-molecules. Factor XIII is isolated from human or bovine blood or placenta; however, in application for human treatment, it is preferable to use Factor XIII derived from human sources. Factor XIII and thrombin can be fixed by bonding or adsorbing in the carrier, and for bonding, it is possible to adopt the conventionally well known covalent bond or ionic-bond, as described in O. Zaborsky, *Immobilized Enzyme,* CRC Press, 1973.

For covalent bond of carrier with Factor XIII and thrombin, among the methods that may be used are: (1) use of dehydrating condensation agents such as dicyclohexyl carbodiimide, 1-cyclohexyl-3-(2-morpholinoethyl)-carboimide-metho-toleune sulphonate, etc.; (2) treatment with Factor XIII and thrombin after introducing a formyl group by the treatment of the carrier with glutaric aldehyde or polyaldehyde such as dialdehyde-starch, etc.; (3) introduction into the carrier with a chlorotriadzinyl group by cyanul chloride, an epoxy-group by polyglycidyl derivatives such as ethylene glycol, tetramethyl glycol, glycerin, etc., an isocyanate-group by polyisocyanates such as toluene diisocyanate, hexamethylene diisocyanate, etc., an acid anhydride group by maleic acid polyanhydrides such as copolymers of maleic acid anhydride, an iminocarbonate group and a bromo-acetyl group by bromocyan instead of polyaldehyde. By such methods, it is possible to adopt the bonding methods of thrombin and Factor XIII by the use of function group formable of these covalent bonds.

For ionic bond of thrombin and Factor XIII with the carrier, it is possible to use the carboxyl group of the carrier, or as mentioned above, the carrier introduced with a formyl group, an imino-carbonate group, a bromo-acetyl group, an acid anhydride group, an isocyanate group, an epoxy group, a chlorotriadzinyl group, is aminated by the treatment with polyamines such as polyethylene imine, etc., and it is carboxylated by the treatment with aminocarboxylic acids such as glycine, etc., therefore, ionic bond can be made for thrombin and Factor XIII with the carrier introduced with a carboxyl group and an amino-group as ion-exchange group. Among these, a favorable method is ionic-bonding with an amino group of thrombin and Factor XIII by the use of a carboxyl group possessed by the carrier, from the viewpoint of less inactivating degree for thrombin and Factor XIII.

For adsorption of Factor XIII and thrombin into the carrier by physical adsorption method or entrapping method, it is possible to perform procedures as described below.

The carrier-wettable solvent can be mixed with Factor XIII and thrombin for dissolution, and carrier is treated by the resultant solution and, as a result, Factor XIII and thrombin can be adsorbed physically. Under the mixed aqueous solution state, activity loss of Factor XIIIa (activated Factor XIII by thrombin) is so fast, thus it is better to suppress the treating time to not more than about 10 minutes, and preferably the treating time is from 3 to 5 minutes. As solvent, water is preferably used, and the most preferably adopted method in all fixing methods is to treat the carrier by aqueous solution of thrombin and Factor XIII. Also, the temperature of aqueous solution is preferably not more than 15° C., and more preferably is from 0° to 7° C., because as the temperature of the solution increase activities of thrombin and Factor XIII decreases. The entrapping method covers Factor XIII and thrombin in micro-fine lattices of gel for inhibiting disconnection from the carrier.

In either fixing method for Factor XIII and thrombin by the above mentioned methods, Factor XIII and thrombin may be simultaneously fixed, or Factor XIII may be fixed firstly, followed by fixation of thrombin. In the latter method, the order of the Factor XIII and thrombin to be fixed is not limited. Also, by previous and separate manufacture of the fixed Factor XIII and thrombin, these materials may be mixed or laminated. Moreover, upon manufacturing the hemostatic agent of this invention, it is possible to fix Ca-ion related to the activation of Factor XIII for the carrier. Further, for the manufacture of hemostatic agent of this invention, if desired, it is possible to fix drugs such as anti-plasmin agents, bacteriocides, antibiotics, hormones, and anti-cancer agents with the carrier as with the Factor XIII and thrombin. There is no particular limitation on the amounts of thrombin and Factor XIII fixed on the carrier, but for instance, in the use as hemostatic agent for the bleeding after biopsy in man, the amount of thrombin would generally be from 0.1 to 5000 units, preferably from 1 to 10000 units per injection, more preferably from 10 to 5000 units, and most preferably from 75 to 750 units. As to the amount of Factor XIII, the amount would generally be from 0.001 to 50000 units per injection, preferably from 0.01 to 5000 units, more preferably from 0.25 to 1000 units and most preferably from 2 to 350 units.

In exceeding 50000 units of Factor XIII and thrombin, no-increase of hemostatic effect is obtained, and side effects may appear. Also, insufficient hemostatic effect may be obtained by using less than 0.1 unit and 0.001 unit, respectively. The desirable amount of hemostatic agent of this invention per injection is generally from 1 to 5000 mg, preferably from 10 to 1000 mg, and more preferably 50 to 500 mg. The injection of an amount exceeding 5000 mg will induce higher burden against the tissue of injecting site, while an injecting amount less than 1 mg shows insufficient hemostatic effect. The desirable fixing amount of thrombin to the carrier is from 0.001 to 1000 units per mg, more preferably from 0.05 to 50 units per mg and most preferably from 0.5 to 5 units per mg. The desirable fixing amount of Factor XIII to the carrier is generally from 0.0001 to 100 units per mg, preferably from 0.001 to 10 units, and most preferably from 0.01 to 2.5 units per mg.

It is difficult to make uniform fixation of Factor XIII and thrombin with carrier in exceeding 100 and 1000 units per mg respectively. Even if fixation is made, hemostatic effect is not so elevated, and rather, it is unfavorable in considering the possibility of increasing side effects by the administration of drugs in more than a necessary amount. Moreover, hemostatic effect is insufficient at the amounts of less than 0.01 unit per mg and 0.001 unit per mg, respectively. The hemostatic effect is lower by fixing thrombin alone or Factor XIII alone. Synergistic effects can be obtained by fixing both simultaneously.

The hemostatic agent of this invention is usually filled in a vial and an ampule made of glass or plastic material which are available for packing of medicine, and after sol-formation by the media such as water, etc., at the time of use, it is used by suction into a syringe. More particularly, it is conveniently injectable by connecting a syringe with puncture needle or biopsy needle after sol-formation in a syringe by inducing a liquid medium such as physiological saline solution, distilled water for injection or aqueous calcium chloride solution from the outside after filling the hemostatic agent in the syringe initially.

Moreover, it is possible to conduct automatic mixing for this hemostatic agent by the invention with physiological saline solution, etc., by the action in breaking the negative pressure (i.e., lower than atmospheric pressure) at the time of use after previous setting of the container at negative pressure when being filled with hemostatic agent of this invention. The sol-concentration of the agent is generally from 5 to 500 mg/ml, preferably from 10 to 250 mg/ml, and more preferably from 20 to 150 mg/ml. The hemostatic effect tends to be insufficient at a sol-concentration less than 5 mg/ml, whereas a sol-concentration over 500 mg/ml is too thick to be uniform or homogenous for use, or it is difficult for injection by a fine needle.

Hemostatic agent by this invention is most favorably used with the best hemostatic effect against bleeding after an operation with direct puncture or biopsy, and prompt hemostasis can be obtained thereby. Moreover, even conventionally inoperable cases with an increasing tendency toward bleeding by preoperative tests can be treated by the use of the hemostatic agent of the present invention. Moreover, the hemostatic agent by this invention exerts its efficacy for ordinary hemorrhage, namely, the bleeding by both surgical treatments and injuries. As in the following, detailed explanation is made on this invention with reference to examples.

EXAMPLE 1

Biodegradable powder gelatin (200 mg) {Gelform powder (product of Upjohn) with water-absorption capability of 500–800 weight percent, mixture of flake substance in its longest dimension from 20 $\mu$m to 200 $\mu$m} was soaked in 4 ml of mixture aqueous solution consisting of 3 ml of aqueous solution of thrombin powder {condensed dry preparation of human thrombin (product of Green Cross), dissolving 1 bottle thereof (500 units) in 5 ml of water.} and 1 ml of aqueous solution of fibrogamin {condensed dry preparation of Factor XIII (product of Hoechst, Behling Institute), dissolving 1 bottle in 25 ml of water.} for 2 minutes at 0° C. Thereafter, by freezing and drying at −60° C. for 30 hours, powder-gelatin was fixed with thrombin and Factor XIII by ionic-bonding and physical adsorption, and thus the hemostatic agent was obtained.

The adsorbed amount of thrombin was about 300 units/300 mg and that of Factor XIII was about 10 units/200 mg. 3000 units/kg of heparin (Novo Heparin Inj., products of Novo Ind. A/S) was injected caudal venously in female rats (Crj; Spracue-Dawley rat, body weight about 500 g), and hepatic biopsy was performed by the use of a biopsy-needle (product of Top Co., Ltd., thin type, outer needle-thickness 1.70 mm, length 72.5 mm; inner needle thickness 1.40 mm). Immediately thereafter, distilled water for injection 0.1 ml was infused into the syringe in which 2 mg of the hemostatic agent previously prepared filed, and this syringe was mounted with outer cylinder of biopsy needle, then, while slowly drawing the outer cylinder, gel-formed hemostatic agent was infused. After drawing out the outer cylinder, bleeding was observed, thus the time up to hemostasis was measured, and the similar test was performed for 6 rats. As a result, the time until hemostasis was 32, 5, 4, 35, 2 and 18 seconds for the individual rats.

COMPARATIVE EXAMPLE 1

Hepatic biopsy was performed for other 6 rats similar to Example 1. However, hemostatic agent was not infused as in Example 1, and compression hemostatic was performed by the use of ordinary sounding, then, the measured time until hemostasis was 540, 560, 590, 480, 390 and 420 seconds for the individual rats.

EXAMPLES 2-5 AND COMPARATIVE EXAMPLES 2-6

Heparin (Novo Heparion Inj. (Novo Ind. A/S) 7500 units/kg was caudal venously injected in female rats (Crj; Spracue-Dawley Rat, body weight about 200 g), then, hepatic biopsy was performed by the use of biopsy needle (Silverman Biopsy Needle, outerdiameter 3 mm, length 20 cm), immediately thereafter, distilled water 0.5 ml was infused into the syringe filled with 10 mg of hemostatic agent prepared by the producing method based on Example 1 as shown in Table 1, and after making it sol-formation, this syringe was mounted on the outer cylinder of biopsy-needle, and sol-agent was injected into the site of biopsy. Immediately after injection, outer cylinder of biopsy needle was drawn out, and the time up to hemostasis was measured. Similar test was performed in 3 rats, and the results are shown in Table 2.

TABLE 1

| Example No. | Used Hemostatic Agent | |
|---|---|---|
| | Thrombin (unit)* | Factor XIII (unit)* |
| Comparative Example | | |
| 2 | 0 | 0 |
| 3 | 75 | 0 |
| 4 | 750 | 0 |
| 5 | 0 | 2 |
| 6 | 0 | 350 |
| Example | | |
| 2 | 75 | 2 |
| 3 | 750 | 2 |
| 4 | 75 | 350 |
| 5 | 750 | 350 |

Note. *For powder gelatin 150 mg, fixed thrombin units, and Factor XIII units

TABLE 2

| | Time Needed for Hemostasis | | | Mean Value by 3-Times Test (second) |
|---|---|---|---|---|
| | Rat No. 1 (second) | Rat No. 2 (second) | Rat No. 3 (second) | |
| Comparative Example | | | | |
| 2 | 998 | 864 | 873 | 912 |
| 3 | 762 | 728 | 878 | 789 |
| 4 | 712 | 645 | 700 | 686 |
| 5 | 884 | 813 | 892 | 863 |
| 6 | 853 | 721 | 780 | 785 |
| Example | | | | |
| 2 | 244 | 213 | 224 | 227 |
| 3 | 193 | 246 | 184 | 208 |
| 4 | 239 | 203 | 194 | 212 |
| 5 | 168 | 192 | 236 | 199 |

As shown in Table 2, hemostatic time was remarkably long when both thrombin and Factor XIII showed "O", or either one showed "O" (i.e., in the comparative examples). While hemostatic time is extremely shortened when both exist. This fact shows that the hemostatic effect of the hemostatic agent of this invention shows a synergistic effect by the combination of thrombin and Factor XIII.

EXAMPLE 6

May pack (a temporary or emergency covering material for a cutaneous defect, which is a atherocollagen fiber aggregation, produced by Meiji Seika) was minced in a homogenizer, and 200 mg of fiber aggregation consisting of fiber with a maximum length of 2.5 mm with the single yarn fineness of maximum 10 deniers could be obtained, and its water-absorption capability was 98-weight percent. This substance was soaked in a mixture solution consisting of 5 ml of aqueous solution of thrombin powder condensed dry preparation of human thrombin (product of Green Cross), dissolving 2 bottles thereof (1000 units) in water 5 ml and 5 ml of aqueous solution of fibrogamine {condensed dry preparation of Factor XIII (Hoechst, Behling Laboratories), dissolving 2 bottles in water 5 ml} for one minute at 4° C. Thereafter, the substance was frozen and dried at −40° C. for 20 hours, and thus the hemostatic agent with Factor XIII fixed at about 2.5 units and thrombin fixed at about 5 units per mg of Maypack was obtained. This hemostatic agent 38 mg was formed into "sol" by 0.5 ml $CaCl_2$ (2-weight percent), and it was injected into rats for hemostatic testing as in Example 1. The observed time until hemostasis was obtained were 13, 31, 4, 30, 4 and 3 seconds for the six individual rats tested.

EXAMPLE 7

Oxycellulose cotton (absorbable oxidized cellulose cotton type, product of Sankyo Co., Ltd.) 200 mg was washed in aqueous solution 200 ml of 0.5N-calcium acetate at room temperature for 2 hours, followed by washing with water. Then, it was dried in air, and thus neutral oxycellulose cotton was obtained. This substance was a fiber aggregation consisting of fiber with water-absorption capability of 65 weight percent, and a fiber length maximum of 1500 microns and single-fiber fineness maximum of 3 deniers. Treated in a manner analogous to Example 1, a substance with Factor XIII fixed at about 0.5 unit and thrombin fixed at about 1.5 unit per mg of neutralized oxycellulose cotton was obtained. This substance was combined at an amount of 40 mg with 1 ml of physiological solution, whereby, after 10 seconds, a uniform sol-form was obtained. The resultant sol smoothly passed through a B 23G-syringe needle.

COMPARATIVE EXAMPLE 7

From oxycellulose cotton as used in Example 7, the material with a fiber length over 15 mm was collected. Then, as analogous operation was made as in Example 7, except for the neutralizing operation by calcium acetate, and thus oxycellulose cotton fixed with Factor XIII and thrombin was obtained. Using this fixed oxycellulose cotton, the analogous test to that of Example 7 for passing through the needle of the syringe was conducted. However, no uniform sol was obtained, and the sol was not easily passed even through an 18G-needle.

While this invention has been described in detail and with reference to specific embodiments thereof, it will be apparent to one skilled in the art that various changes and modifications can be made therein without departing from the spirit and scope thereof.

What is claimed is:

1. A hemostatic agent comprising a carrier in the shape of individual, separate flake or fiber having thrombin and Factor XIII fixed thereto, wherein said carrier is composed of a biodegradable material having a water absorption capability of about 50 weight percent or more, said flake has a longer dimension of about 5,000 microns or less, a shorter dimension of about 3,000 microns or less, and a thickness of about 2,000 microns or less, and said fiber has a single yarn fineness of about 30 deniers or less and a yarn length of about 10 mm or less.

2. A hemostatic agent as in claim 1, wherein a sol-form is provided for administration into bleeding sites by mixing with a liquid medium selected from physiological saline solution, distilled water for injection or aqueous calcium chloride solution.

3. A hemostatic agent as in claim 1, wherein said agent is usable for hemostasis at a site where bleeding is caused by puncture or biopsy.

4. A hemostatic agent as in claim 1, wherein the water absorption capability is less than 1000 weight percent.

5. A hemostatic agent as in claim 1, wherein the carrier material is selected from the grown consisting of collagen, gelatin, chitin, fibrinogen, polyglycolic acid, polylactic acid, glycolic acid-lactic acid copolymer, polyglutamic acid, amylose and oxidized amylose.

6. A hemostatic agent as in claim 1, wherein the flake has a longer dimension of 200 to 1000 microns, a shorter dimension of 200 to 800 microns, and a thickness of 800 microns or less, and the fiber has a single yarn fineness of 0.5 to 15 deniers and a yarn length of less than 3 mm.

7. A hemostatic agent as in claim 1, wherein in the use as hemostatic agent for the bleeding after biopsy in man, the amount of thrombin is 0.1 to 50000 units and the amount of Factor XIII is 0.001 to 50000 units, per injection.

8. A hemostatic agent is in claim 1, wherein the fixing amount of thrombin to the carrier is 0.001 to 1000 units per mg and the fixing amount of Factor XIII to the carrier is 0.0001 to 100 units per mg.

9. A method comprising mixing a hemostatic agent with a liquid medium to obtain a sol-form, and administering said sol-form to a bleeding site, said hemostatic agent comprising a carrier in the shape of individual, separate flake or fiber having thrombin and Factor XIII fixed thereto, wherein said carrier is composed of a biodegradable material having a water absorption capability of about 50 weight percent or more, said flake has a longer dimension of about 5000 microns or less, a shorter dimension of about 3000 microns or less, and a thickness of about 2000 microns or less, and said fiber has a single yarn fineness of about 30 deniers or less and a yarn length of about 10 mm or less.

10. A method as in claim 9, wherein administration is performed through a puncture needle or a biopsy needle.

11. A method as in claim 9, wherein the concentration of said hemostatic agent in the sol-form is from 5 to 500 mg/ml.

12. A method as in claim 9, wherein the amount of hemostatic agent per injection is 1 to 5000 mg.

* * * * *